Figure 6:
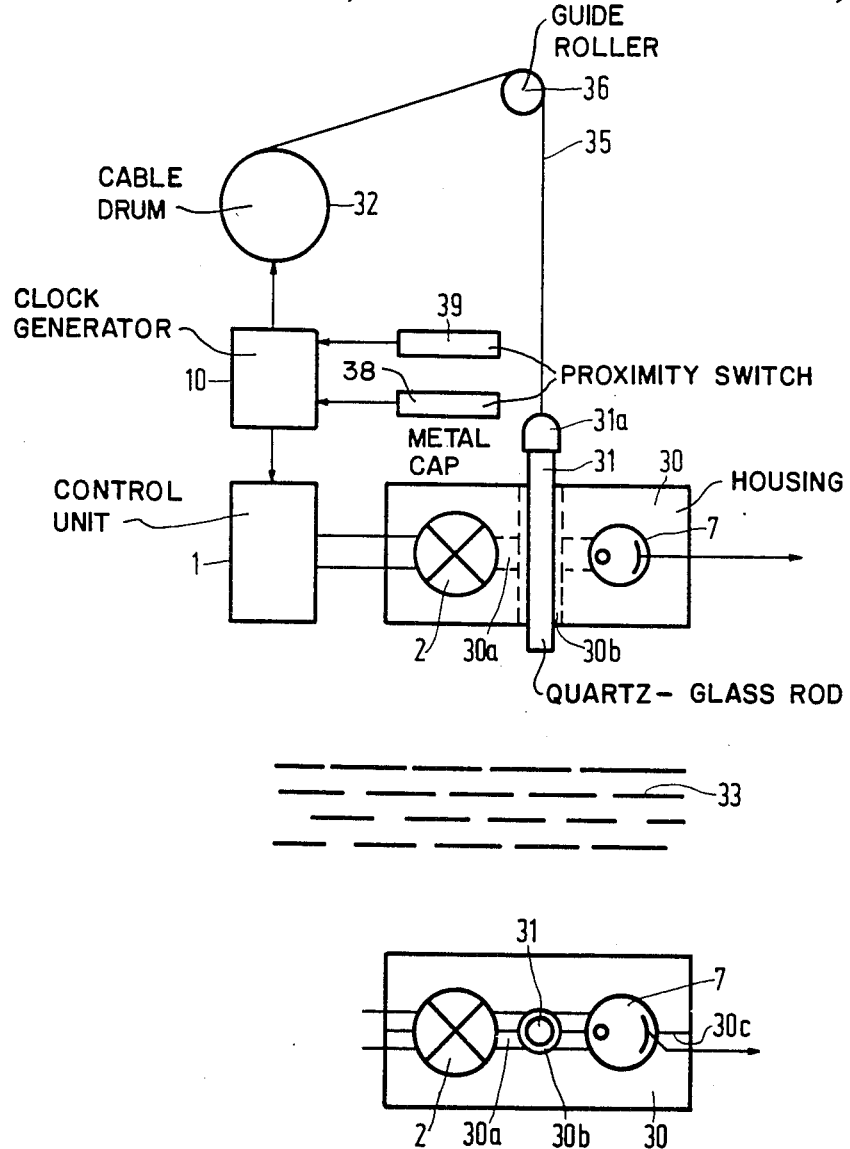

United States Patent [19]

Harig et al.

[11] Patent Number: 4,622,465
[45] Date of Patent: Nov. 11, 1986

[54] ARRANGEMENT FOR DETERMINING THE PRESENCE OF SPECIFIC SUBSTANCES IN A LIQUID

[75] Inventors: Egon H. A. Harig; Gerd H. Martens, both of Hamburg, Fed. Rep. of Germany

[73] Assignee: U.S. Philips Corporation, New York, N.Y.

[21] Appl. No.: 600,676

[22] Filed: Apr. 16, 1984

[30] Foreign Application Priority Data

Apr. 28, 1983 [DE] Fed. Rep. of Germany ....... 3315443
Feb. 21, 1984 [DE] Fed. Rep. of Germany ....... 3406176

[51] Int. Cl.$^4$ ...................... G01N 21/59; G01N 21/15
[52] U.S. Cl. .................................. 250/373; 250/301; 356/70
[58] Field of Search ................. 250/301, 373, 372; 356/70; 340/603, 627, 631

[56] References Cited

U.S. PATENT DOCUMENTS 3,491,234  1/1970  Wiltrout ............................. 250/373
3,710,111  1/1973  Collura .............................. 250/373
3,731,091  5/1973  Rosso et al. ...................... 250/301

OTHER PUBLICATIONS

Y. Morita et al., "Shimadzu Organic Pollution Monitor Model UVM-401", Shimadzu Review, vol. 37, No. 4, (Dec. 1980), pp. 259-264.

Primary Examiner—Janice A. Howell
Assistant Examiner—Constantine Hannaher
Attorney, Agent, or Firm—Paul R. Miller

[57] ABSTRACT

A simple and sensitive arrangement for determining the presence of specific substances in a liquid is provided for determining the presence of oil in water. The arrangement comprises a light source which emits diffused UV light through the liquid to be tested, a detector which receives the UV light, and a processing circuit which is driven with a measured signal from the detector. The processing circuit generates an alarm signal if the measurement signal which increases with intensity of the detected UV light becomes smaller than the predetermined value.

13 Claims, 6 Drawing Figures

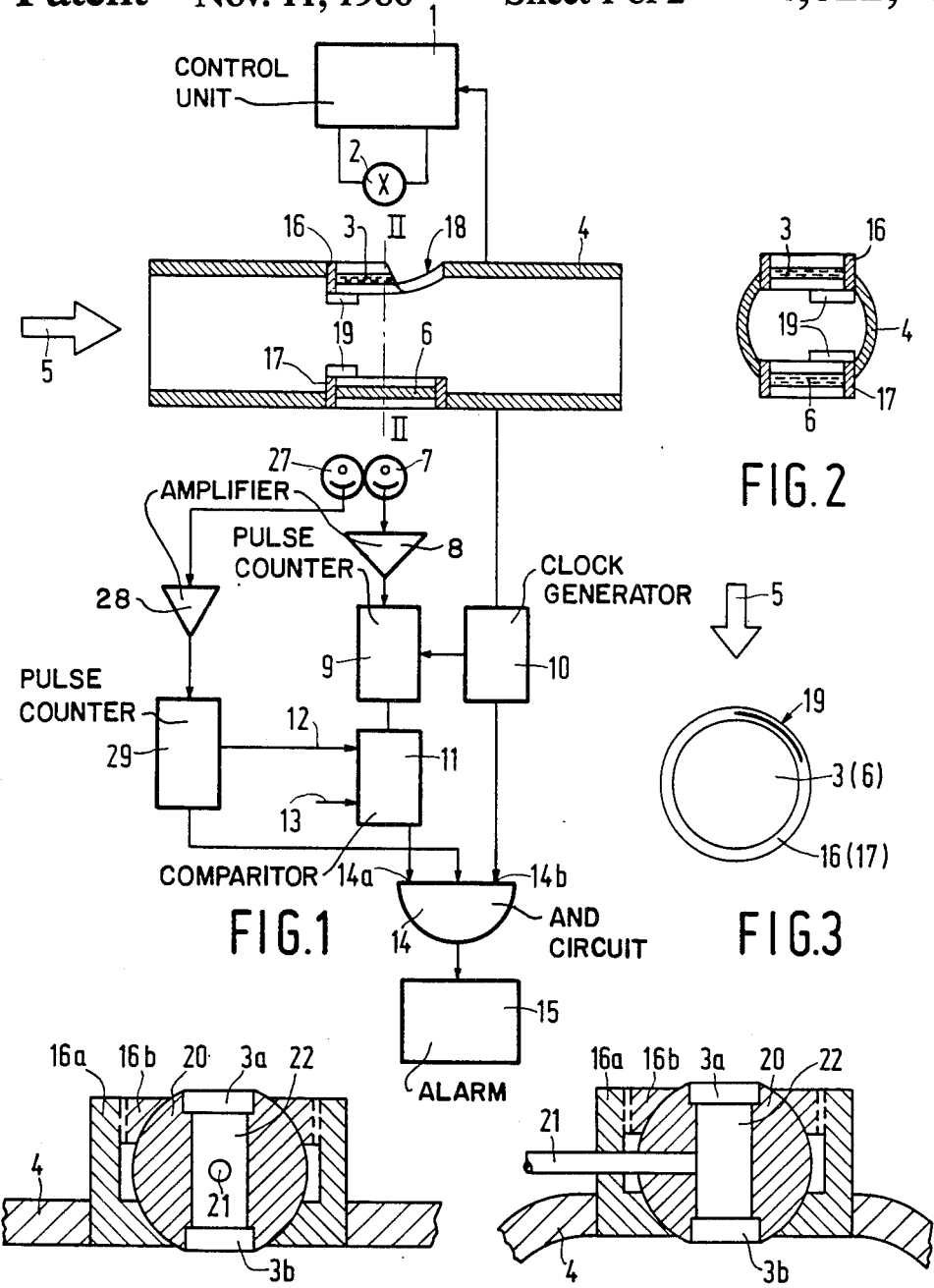

ARRANGEMENT FOR DETERMINING THE PRESENCE OF SPECIFIC SUBSTANCES IN A LIQUID

The invention relates to an arrangement for determining the presence of specific substances in a liquid, in particular the presence of oil in water, by means of a light source with the light emitted by the light-source and transmitted by the liquid being received by a light detector which supplies a measurement signal whose value increases with the light intensity to a processing circuit.

DE-OS No. 27 15 118 discloses an arrangement for determining the oil content of water, in which arrangement different samples of the liquid to be tested are emulsified to different extents by means of an emulsifier device which is alternately switched to different driving powers, after which the samples are exposed to visible light. By means of a processing circuit the oil content of the water is calculated from the turbidity signals derived from the samples which have been emulsified to different extents. Since water which is rendered turbid by the emulsified oil attenuates in particular collimated light, a collimator is arranged between the light source and the measurement cell in the known arrangement. Therefore, the known arrangement for determining the oil content of water is very intricate. Moreover, since the light is attenuated only if the water contains emulsified oil in a comparatively high concentration, the known arrangement does not permit the measurement of low oil concentrations in water.

It is the object of the present invention to provide a simple and sensitive arrangement for determining the presence of specific substances in a liquid, in particular for determining the presence of oil in water.

According to the invention this object is achieved in that the light source emits diffuse light with UV components, the detector is sensitive to at least UV light, and the processing circuit generates an alarm signal when the measurement signal becomes smaller than a predetermined value.

Oil which is present in the water in a low concentration attenuates UV light by absorption instead of by scattering, so that a collimator for concentrating the light transmitted through the liquid is not required. This simplifies the processing circuit because the oil content of the water is not calculated but merely an alarm signal is generated if the oil content exceeds a specific value.

Examining liquids by means of UV light in order to determine their compositions is known from analysis technology. For this purpose the liquid to be tested is consecutively exposed to UV light in successive spectral ranges with the composition of the liquid being determined from the spectral dependence thus found of the light attenuation by the liquid to be tested. However, this known method can be used only under laboratory conditions and for reasons of economy it cannot be used for continuously testing whether the content of specific substances such as oil in, for example, water exceeds a specific value.

In particular for determining the presence of oil in water it is effective if the light source emits light mainly in a range of wavelengths from 0.2 to 0.3 $\mu$m. This enables even low concentrations of oil to be detected. A narrow band of wavelengths around 0.23 $\mu$m is found to be particularly favourable.

In a further advantageous embodiment of the invention the light detector is a phototube which generates a train of pulses whose pulse frequency increases with the light intensity, and the pulses are counted by a pulse counter which is set to a first preset value at the beginning of a measuring interval and which activates an alarm means when the pulse counter has not reached a second preset value at the end of the measuring interval. The use of such a pulse counter yields very reliable and accurate measuring results.

In a further embodiment of the invention the arrangement comprises a clock generator which resets the up-counting pulse counter to zero at the beginning of each measuring interval and which drives a comparator circuit at the end of each measuring interval. The comparator circuit compares the count of the pulse counter with the second preset value and supplies a trigger signal to the alarm means if the count of the pulse counter at the end of the measuring interval is smaller than the second preset value. The processing circuit then operates automatically because it is controlled by a clock generator.

In a further embodiment of the invention the comparator circuit comprises a comparator which compares the count of the pulse counter with the second preset value and supplies a comparison signal to a first input of an AND-circuit if the count is smaller than the second preset value, and the clock generator drives a second input of the AND-circuit at the end of each measuring interval with an output of the AND-circuit being connected to the alarm means. By means of the AND-circuit it is possible in a simple manner to ascertain whether the comparator signals that the count which corresponds to a specific degree of oil pollution of the water does not reach a predetermined value.

Since the phototube also produces pulses in the case of radioactive radiation, the arrangement in accordance with the invention is also suitable for checking water for the presence of radioactive substances if the pulses supplied by the phototube are counted and processed while the light is switched off. Therefore, it is effective if a measurement pause of predetermined length is situated between every two measuring intervals, the light source, under control of the clock generator, only emits light during the measuring intervals, and the pulse counter, which has been set to the first preset value at the beginning of the measurement pause, counts the pulses supplied by the light detector until the end of the measurement pause and activates the alarm means if the pulse counter has reached a third preset value at the end of the measurement pause.

In many cases it is possible that, for example, water contains other substances which can be detected more readily than oil. Such substances may be, for example, suspended substances which not only attenuate UV light but which also attenuate visible light. In order to distinguish the attenuation of UV light in such cases from that as a result of the presence of oil and to preclude a false alarm, it is effective if the light source also emits light in a range of longer wavelengths, if there is also provided a further light detector which is sensitive to the longer wavelengths and a further processing circuit, which supplies a further measurement signal depending on the intensity of the light received by the further light detector, and if the further measurement signal sets the processing circuit for the alarm to a less sensitive setting or disables the alarm means if the intensity of the light which is incident on the further light detector becomes smaller than a predetermined value. If desired, the further processing circuit may provide an indication of the attenuation, for example when a threshold value is exceeded. Alternatively, the light of long wavelength may be produced by an additional light source.

In a further embodiment of the invention the liquid to be checked flows through a metal tube provided with quartz windows arranged between the light source and the light detector. This embodiment of the invention can be manufactured cheaply and is resistant to aggressive ambient conditions.

The metal tube may comprise projections which render the liquid in front of the quartz windows turbulent. They distribute the oil in the water and prevent the oil from settling on the quartz windows.

A deposit of oil or other substances on the quartz windows cannot be precluded entirely after prolonged operation, so that the UV light or, as the case may be, the visible light is also attenuated without the substances being actually present in the liquid in corresponding concentrations, which may give rise to the alarm means being triggered erroneously. In order to avoid this the quartz windows have to be cleaned at regular intervals. However, this is very difficult and intricate if the measurement cell is rigidly mounted in a pipeline system. In order to enable the quartz windows to be cleaned easily, it is effective if the quartz windows are arranged in the metal tube in spherical mountings which are fitted in a hollow spherical holder in a pressure-tight manner, which holder is rotatable about a shaft substantially tangential to the metal tube. By rotating the spherical holder, it is possible to gain access to the quartz window or windows for cleaning purposes without interrupting the liquid flow and hence the operation of the arrangement.

If it is required to test a liquid containing a substantial amount of other substances which also give rise to a substantial attenuation of UV light, such as for example domestic or industrial waste water, it is no longer effective to reduce the sensitivity to UV light by measuring the attenuation produced by the substances in a range of longer wavelengths, because this will reduce the sensitivity of the entire measurement, so that it is possible to measure only very high concentrations which lie well above the permissible concentration of, for example, oil in waste water. In order to determine the presence of low concentrations of oil in such liquids it is effective to use a further embodiment of the invention in which a body which is transparent to those UV components to which the detector is sensitive is periodically immersed into and withdrawn from the liquid to be tested and brought in a position between the light source and the light detector by drive means. Here, it is assumed that access to the surface of the liquid to be tested, at least at the testing site, is free and is not impeded by a conduit such as a pipe if the liquid should not flow in a more or less open channel. The periodic immersion leads even to an increased sensitivity because a repeated immersion results in a thicker film of oil on the body and other substances, such as suspended substances, present in the liquid each time drip off. Thus, a low concentration of oil will give rise to a substantial attenuation of the UV light in the test arrangement owing to the repeated immersion. Suitably, the body is a quartz-glass rod. Such a body is highly resistant to most of the aggressive substances such as acids and lyes.

Periodic immersion and withdrawal of the body can be effected for example by means of a motor-driven mechanism. However, a particularly simple construction is obtained in a further embodiment of the invention which is characterized in that the body is suspended from a wire or cable which is periodically taken up by and unwound from a motor-driven cable drum constituting the drive means. This results in a very simple yet reliable arrangement.

In order to guarantee that in the withdrawn position during the measurement cycle the body is situated at the correct location it is effective if a proximity switch is so arranged that it is activated when the body is in the correct position between the light source and the light detector. This proximity switch may then control the drive means.

Embodiments of the invention will now be described in more detail, by way of example, with reference to the drawings. In the drawings FIG. 1 shows schematically the arrangement in accordance with the invention, FIG. 2 is a sectional view of the measuring cell taken on the line II—II, FIG. 3 is a plan view of a quartz window, FIG. 4 is a sectional view of the measuring cell with different mountings of the quartz windows, FIG. 5 is a sectional view of the measuring cell in a direction perpendicular to that in FIG. 4, and FIG. 6 shows an arrangement for testing a liquid by means of a periodically immersed body.

In FIG. 1 the light source 2, which can be controlled by the light source control unit 1, is arranged in front of the quartz window 3 and transilluminates the liquid which flows in a measuring cell 4 in a direction indicated by the arrow 5 with diffuse light which comprises mainly UV components in the range of wavelengths from 0.2 to 0.3 $\mu$m, in particular around 0.23 $\mu$m. The light traverses the quartz windows 3 and 6 and is incident on the light detector 7 in the form of a phototube. The measurement signal supplied to the pulse counter 9 via the amplifier 8 by the light detector 7 comprises a pulse train whose pulse frequency increases depending on the intensity of the light which is incident on the photodetector 7. At the beginning of each measuring interval the pulse counter 9 is set to a first value, in particular zero, by the clock generator 10. The comparator 11 compares the count of the pulse counter 9 with values which are applied by mechanical or electrical input means via the inputs 12 and 13. A comparison signal from the comparator 11 is applied to a first input 14a of an AND-circuit 14. At the end of each measuring interval the clock generator applies a pulse to the second input 14b. When a signal is present on both inputs 14a and 14b of the AND-circuit 14 the AND-circuit 14 supplies a trigger signal to the alarm means 15, which then generates a signal which is perceptible to an operator, which signal indicates that the oil content of the liquid which flows through the measurement cell 4 exceeds a preset value. The light-source control unit 1 is controlled in such a manner by the clock generator 10 that the light source 2 emits light in the measuring interval only. Suitably, the clock generator 10 is self-checking, so that in the event the clock pulses do not appear a corresponding alarm signal is generated because the liquid is no longer tested in this situation.

The attenuation of the light emitted by the light source 2 increases as the liquid which flows through the mesurement cell 4 contains more oil. The attenuated light is incident on the phototube 7 which supplies a measurement signal in the form of a train of pulses whose pulse frequency decreases as the attenuation of the UV containing light with which the liquid is transilluminated increases. The pulse counter 9, which is reset to zero by a short pulse from the clock generator 10 at the beginning of every measuring interval, counts the pulses supplied by the photo tube 7. The pulse counter 9 supplies an analog or digital signal representing the count to the comparator 11, which compares this signal with a further signal applied to the input 12. The comparator applies a signal to the input 14a of the AND-circuit 14 as long as the count of the upcounting pulse counter 9 is smaller than the preset value which can be applied via the input 12. Only if the liquid which flows through the measurement cell 4 is not contaminated with other substances will the phototube 7 receive enough light and the frequency of the measurement signal supplied to the pulse counter 9 by the photo tube 7 will be so high that the pulse counter 9 reaches the preset value before the measuring interval has terminated and supplies no signal to the AND-circuit 14 at the end of the measuring interval. If at the end of the measuring interval the AND-circuit 14 then receives a signal from the clock generator 10 a signal will appear on input 14b but not on input 14a, so that the AND-circuit 14 will not supply a trigger signal to the alarm means.

If due to contamination of the liquid with oil and the resulting light attenuation the pulse counter 9 counts too slowly, the pulse counter 9 will not reach the preset value at the end of the measuring interval and the comparator 11 will supply a comparison signal to the input 14a until the end of the measuring interval. Therefore, if at the end of the measuring interval the clock generator 10 also supplies a signal to the input 14b, the AND-circuit 14 will generate the trigger signal which is applied to the alarm means to produce an alarm signal. Alternatively, instead of the AND-circuit 14 a D-flip-flop may be employed, whose D-input receives the output signal of the comparator 11 and whose clock input receives the clock signal from the clock generator 10.

Alternatively, the pulse from the clock generator may set the pulse counter 9 to a count which differs from zero and which corresponds to the signal on the input 12 and the pulse counter may, for example, count down. A signal representing the final count of the counter may then be applied directly to the AND-gate 14, so that the comparator 11 may be dispensed with.

Between the signals applied to the pulse counter 9 at the beginning of the measuring interval and to the AND-circuit 14 at the end of the measuring interval the clock generator 10 supplies a signal to the light-source control unit 1 in order to ensure that the light-source control unit 1 only switches on the light source 2 during the measuring intervals. Between the measuring intervals longer measurement pauses may occur in which the light source 2 does not emit light in order to extend the life of the light source 2.

In the measurement pauses the arrangement may be used for checking a liquid for the presence of radioactive substances, because the phototube 7 also emits pulses when exposed to radioactive radiation. These pulses are counted by the pulse counter 9 which has been reset to zero by the clock generator 10 at the beginning of the measurement pause. The comparator 11 is constructed to supply a signal to the input 14a of the AND-circuit 14 only if the pulse counter 9 exceeds a third value which can be preset by means of the input device 13. If the third value is exceeded at the end of the measurement pause the liquid will contain radioactive substances. Therefore, if at the end of the measuring interval the clock genrator 10 also supplies a pulse to the input 14b of the AND-circuit 14, the AND-circuit 14 will supply a trigger signal to the alarm means 15 to produce an alarm. The processing circuit may comprise a downcounting pulse counter 9 which is set to a first value which differs from zero at the beginning of each measuring interval. The comparator 11 is then constructed to supply a signal to the input 14a of the AND-circuit 14 as long as the down-counting pulse counter 9 has not reached the second value for example zero, entered via the input 12.

The embodiment shown in FIG. 1 further compriss a further light detector 27 for light of a longer wavelength preferably for visible light, assuming that the light source 2 also emits visible light. On the other hand, there may be provided an additional light source. The output signal of the further light detector 27, which for the sake of simplicity is also assumed to be pulse-shaped, is applied to a further pulse counter 29 via an amplifier 28, which further pulse counter is also set to zero by a pulse from the clock generator at the beginning of every measuring interval in the same way as the pulse counter 9.

By the input 12 the count of the further pulse counter 29 may be applied to the comparator 11 as a further comparison signal, instead of an extremely preset fixed signal. It is then assumed that normally the pulse frequencies of the signals from both light detectors 7 and 27 are substantially equal, but alternatively a coarse adaptation can be achieved by shifting the bits of the digital signal. Thus, if the visible light is attenuated by, for example, suspended substances the threshold value for the comparator 11 is reduced, and the pulse counter 9 supplies a signal to the AND-circuit at the end of the measuring interval when this threshold value is not reached.

Another possibility is that the input 12 of the comparator 11 receives a constant signal and an output of the further pulse counter 29, for example the output of the most-significant stage or the carry output, is connected to a further input 14c of the AND-circuit 14. If the attenuation of the visible light becomes too high, the further pulse counter 29 does not count to the end of the measuring interval to enable the AND-circuit, so that no alarm will be given.

A further circuit corresponding to the comparator 11, the AND-circuit 14 and the alarm means 15 may be connected to the further pulse counter 29 in order to indicate a visible turbidity of the liquid to be tested, as a sign that now the presence of oil does not give rise to an alarm signal.

FIG. 2 is a sectional view of the measurement cell 4 at the location of the quartz windows 3 and 6, which are preferably mounted in metal frames 16, 17 to facilitate mounting of the quartz windows 3 and 6 in the measurement cell 4 which is preferably made of a metal. By means of the frames 16 and 17 the quartz windows 3 and 6 can be mounted in the bores 18 of the measurement cell 4, for example by screwthread, welding or by means of an adhesive. Furthermore the frames 16 and 17 may be provided with device 19 which, as is shown in FIG. 3, may be constructed, for example, as strip-shaped fins which render the liquid flowing in the direction 5 in front of the quartz windows 3 and 6 turbulent.

Another construction for mounting the quartz windows in the measurement cell is shown in FIGS. 4 and 5, in which only part of the upper tube wall is shown. The frame 16 comprises two parts, the main frame 16a and a screwed-in ring 16b, which together form a hollow spherical holder in which a spherical part 20 is mounted in a pressure-tight but rotatable manner. The shaft 21 for rotating the spherical part 20 projects from the tube 4. The spherical part 20 is formed with the bore 22, of which both ends are closed by a quartz window 3a and 3b respectively. If during operation deposits on the quartz windows have to be removed, the quartz window 3a is cleaned, subsequently the spherical part 20 is rotated through 180° about its axis of rotation by means of the shaft 21, and finally the quartz window 3b which is then situated at the outside is cleaned. In this way it is not necessary to remove the quartz windows with cleaning being possible during operation.

Other embodiments of the invention are conceivable which do not employ a measurement cell 4 but which only comprise a light source 2, a light detector 7 and a processing circuit and which are mounted in a water-tight housing in such a manner that a free light path is obtained between the light source 2 and the light detector 7. Such test arrangements may be used as freely floating devices, for example to check open water for oil pollution and, as the case may be, radioactive contaminants. If the test arrangement is secured to a float in such a manner that the light source is submerged and the light detector is situated above the water level, the test arrangement is suitable for detecting an oil film which floats on the surface of the water. In the case of an alarm it is then possible to actuate an automatic sampling device.

FIG. 6 shows an arrangement by means of which a liquid such as waste water which is very turbid and which contains substantial amounts of suspended substances and solids can be tested for the presence of small amounts of oil. A cable 35 is secured to a cable drum 32 driven by a motor, not shown, and is guided by a guide roller 36. A metal cap 31a which holds a quartz-glass rod 31 is secured to the other end of the cable 35. In the position shown the quartz-glass rod 31 is located between the light source 2 and the light detector 7. These two elements are arranged in a housing 30 which comprises, for example a plastics block formed with a duct 30b in which the rod 31 can move freely. Moreover, the block has a duct 30a between the light source 2 and the light detector 7, which duct 30a intersects the duct 30b substantially perpendicularly. For maintenance purposes the block 30 is separable along the line 30c, as is shown in the lower part of FIG. 6 which is a sectional view of the duct 30a taken perpendicularly to the plane of the drawing in the upper part of the Figure. This enables for example the front half of the block 30 to be removed in order to remove and replace or clean the light source 2 or the light detector 7 or also the glass rod 31 in the lifted position.

During operation the clock generator 10 controls the cable drum 32 or its associated motor at the beginning of each measuring interval in such a way that the cable 35 is unwound and the quartz-glass rod 31 is lowered into the liquid 33 to be tested. If the cable 35 is secured correctly to the drum 32 and it is completely unwound and continued rotation of the drum 32 will result in the cable 35 being taken up and the quartz-glass rod 31 being withdrawn automatically from the liquid 35. If the metal cap 31a has reached a specific position relative to the proximity switch 38 this switch produces an output signal which is applied to the clock generator to control the light-source control unit 1 in such a way that the light source 2 emits UV light. At the same time the pulses generated by the light detector 7 are applied to the processing circuit as described with reference to FIG. 1. If the liquid 33 contains oil an oil film will be formed on the quartz-glass rod 31 after it has been lifted, which film attenuates the UV light emitted by the light source 2 and incident on the light detector 7. After repeated immersion of the quartz-glass rod 31 during consecutive measuring intervals several layers of oil will settle on the rod 31, causing the attenuation to increase which enables the presence of low concentrations of oil in the waste water to be determined. This merely requires a reversal of the direction of rotation of the cable drum 32 in consecutive measuring intervals, so that in each measuring interval the quartz-glass rod 31 is lowered and subsequently raised without a reversal of the direction of rotation of the cable drum 32 within the measuring intervals. In the clock generator 10 there may be provided a time control which ascertains whether the proximity switch 38 supplies an output signal within a predetermined time interval after lowering has begun in order to detect breakage of the cable 35, failure of the drive of the cable drum 32, or jamming of the rod 31. Above the proximity switch 38 there is arranged another proximity switch 39 which ensures that the drive motor of the cable drum 32 is switched off in the event of failure of the proximity switch 38 so as to preclude damage to the arrangement when taking-up of the cable 35 is not discontinued.

The present embodiment in which a quartz-glass rod suspended from a cable or wire is immersed in the liquid has the advantage that only a small opening for access to the liquid to be tested is required and that the actual test arrangement comprising the light source, the light detector and the processing electronics may be arranged at a location which is remote from the liquid under test. In particular this enables for example ground water at a great depth to be tested for the presence of oil through a narrow bore-hole. Since the test arrangement is located at the surface maintenance is greatly simplified. If this physical separation between the liquid to be tested and the test arrangement is not required it is alternatively possible to employ a basically round quartz disc which is rotated about an axis parallel to the liquid surface and which is immersed partly in order to test a liquid containing large amounts of suspended substances or solid particles. A part of the quartz disc which is situated outside the liquid then revolves between the light source and the light detector. In this way it is achieved that a body, namely every outer part of the quartz disc, is periodically immersed in and withdrawn from the liquid to be tested.

What is claimed is:
1. An arangement for determining the presence of substances in liquids comprising
    a light source emitting diffuse light with UV components,
    container means receiving said diffuse light for containing liquids, said container means passing said diffuse light through said liquids and said container means,
    light detector means receiving said diffuse light passing from said container means for detecting at least UV light and providing a measurement signal having a value increasing with light intensity, said light detector means being at least one phototube, said phototube generating a train of pulses having a pulse frequency increasing with said light intensity, processing circuit means receiving said measurement signal for generating an alarm signal if said measurement signal becomes smaller than a predetermined value, said processing circuit means including at least one pulse counter for counting said train of pulses, said pulse counter being set at a first preset value at the beginning of measuring intervals, and alarm means for providing said alarm signal when said pulse counter fails to reach a second preset value at the end of said measuring intervals.

2. An arrangement according to claim 1, wherein said light source emits light having wavelengths in the range of 0.2 to 0.3 μm.

3. An arrangement according to claim 1 or claim 2, wherein said processing circuit means further includes a clock generator means for resetting said pulse counter to zero at said beginning of said measuring intervals, and a comparator circuit means being driven by said pulse counter at said end of said measuring intervals for comparing counts of said pulse counter with said second preset value, said comparator circuit means supplying a trigger signal to said alarm means if said counts are smaller at said end of said measuring intervals than said second preset value.

4. An arrangement according to claim 3, wherein said comparator circuit means includes a comparator for comparing said count of said pulse counter with said second present value, said comparator supplying a comparison signal to a first input of an AND-circuit if said count is smaller than said second preset value, and wherein said clock generator means drives a second input of said AND-circuit at said end of said measuring intervals, said AND-circuit providing an output signal to said alarm means.

5. An arrangement according to claim 3, wherein a measurement pulse of predetermined length is provided between every two measuring intervals, wherein said light source emits light during said measuring intervals only under control of said clock generator means, and wherein said pulse counter counts pulses supplied by said light detector means until the end of said measurement pulse, said pulse counter being set to said first preset value at the beginning of said measurement pulse, and said pulse counter activating said alarm means if said pulse counter reaches a third preset value at the end of said measurement pulse.

6. An arrangement according to claim 3, wherein said light source also emits light in a range of longer wavelengths, said light detector means including a further phototube sensitive to said range of longer wavelengths, and said processing circuit means includes another pulse counter supplying a further measurement signal, said further measurement signal depending on intensity of light received by said further phototube, and wherein said further measurement signal sets said comparator circuit means to a less sensitive setting or disables said alarm means if light incident on said further phototube has an intensity smaller than a predetermined value.

7. An arrangement according to claim 1 or claim 2, wherein said container means includes a metal tube provided with quartz windows between said light source and said light detector means.

8. An arrangement according to claim 7, wherein said metal tube includes projections to render said liquids between said quartz windows turbulent.

9. An arrangement according to claim 7, wherein said quartz windows are arranged in said metal tube in spherical mountings, said spherical mountings being fitted in a hollow spherical holder in a pressure-tight manner, said holder being rotatable about a shaft substantially tangential to said metal tube.

10. An arrangement according to claim 1 or claim 2, wherein a body being transparent to said UV components is periodically immersed into and withdrawn from said liquids, said body being immersed into said liquids and withdrawn to a position between said light source and said light detector means by a driving means.

11. An arrangement according to claim 10, wherein said body is a quartz-glass rod.

12. An arrangement according to claim 10, wherein said driving means includes a motor driven cable drum and cable periodically taken up or released on said drum, said body being suspended from said cable.

13. An arrangement according to claim 10, wherein a proximity switch is activated when said body is in position between said light source and said light detector means.

* * * * *